(12) United States Patent
Hatton et al.

(10) Patent No.: US 8,921,580 B2
(45) Date of Patent: Dec. 30, 2014

(54) METHODS AND SYSTEMS FOR THE FORMATION OF CYCLIC CARBONATES

(71) Applicant: Massachusetts Institute of Technology, Cambridge, MA (US)

(72) Inventors: Trevor Alan Hatton, Sudbury, MA (US); Timothy F. Jamison, Somerville, MA (US); Jennifer Aiden Kozak, San Francisco, CA (US); Fritz Simeon, Quincy, MA (US); Jie Wu, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/826,539

(22) Filed: Mar. 14, 2013

(65) Prior Publication Data

US 2013/0310575 A1    Nov. 21, 2013

Related U.S. Application Data

(60) Provisional application No. 61/644,709, filed on May 9, 2012.

(51) Int. Cl.
*C07D 317/08* (2006.01)
*C07D 317/38* (2006.01)

(52) U.S. Cl.
CPC .................................. *C07D 317/38* (2013.01)
USPC ........................................ 549/229; 549/228

(58) Field of Classification Search
CPC .................................................... C07D 317/08
USPC ................................................... 549/228, 229
See application file for complete search history.

(56) References Cited

U.S. PATENT DOCUMENTS 6,924,379 B2 * 8/2005 Palanichamy et al. ........ 549/229
2011/0319634 A1 12/2011 North

FOREIGN PATENT DOCUMENTS

WO    WO 2009/109765 A1    9/2009
WO    WO 2010/106324 A1    9/2010

OTHER PUBLICATIONS

Zhang et al (2008): STN International HCAPLUS database, Columbus (OH), accession No. 150: 5626.*
International Search Report and Written Opinion for PCT/US2013/031323 mailed May 21, 2013.
Anderson, Using continuous processes to increase production. Org Process Res Dev. 2012; 16(5): 852-69.
Kozak et al., Bromine-Catalyzed Conversion of $CO_2$ and Epoxides to Cyclic Carbonates under Continuous Flow Conditions. J Am Chem Soc. Nov. 20, 2013 and corresponding Supporting Information. [Epub ahead of print] as well as corresponding supporting information.
Kozak et al., Integrated Electrochemical Processes for $CO_2$ Capture and Conversion to Commodity Chemicals. U.S. Department of Energy National Energy Technology Laboratory Carbon Storage R&D Project Review Meeting. Pittsbutgh, PA. Aug. 21-23, 2012. 30 pages.
North et al., A gas-phase flow reactor for ethylene carbonate synthesis from waste carbon dioxide. Chem Eur J. Nov. 2, 2009;15(43):11454-7. doi: 10.1002/chem.200902436.
North et al., Synthesis of cyclic carbonates from epoxides and $CO_2$. Green Chem. 2010; 12: 1514-39.
Snyder et al., $Et_2SBrSbCl_5Br$: an effective reagent for direct bromonium-induced polyene cyclizations. Angew Chem Int Ed Engl. 2009;48(42):7899-7903, and corresponding Supporting Information. doi: 10.1002/anie.200903834, 87 pages.
Zhang et al. Intramolecularly two-centered cooperation catalysis for the synthesis of cyclic carbonates from $CO_2$ and epoxides. Tetrahedron Letters. 2008; 49: 6589-92.

* cited by examiner

*Primary Examiner* — Golam M M Shameem
(74) *Attorney, Agent, or Firm* — Wolf, Greenfield & Sacks, P.C.

(57) ABSTRACT

Described herein are inventive methods for synthesis of cyclic carbonates from $CO_2$ and epoxide. In some embodiments, the methods are carried out in the presence of a catalyst comprising an electrophilic halogen. In some embodiments, the methods are carried out in a flow reactor.

20 Claims, 5 Drawing Sheets

METHODS AND SYSTEMS FOR THE FORMATION OF CYCLIC CARBONATES

RELATED APPLICATIONS

The present application claims priority under 35 U.S.C. §119(e) to U.S. provisional application, U.S. Ser. No. 61/644,709, filed May 9, 2012, entitled "SYNTHESIS OF CYCLIC CARBONATES AND RELATED SYSTEMS," incorporated herein by reference in its entirety for all purposes.

STATEMENT REGARDING FEDERALLY SPONSORED RESEARCH OR DEVELOPMENT

This invention was made with government support under Grant No. DE-FE0004271 awarded by the US Department of Energy. The government has certain rights in this invention.

FIELD OF INVENTION

Described herein are methods and systems for the formation of cyclic carbonates from $CO_2$ and epoxides.

Anthropogenic carbon dioxide ($CO_2$) from fossil-fuel combustion is cited as the leading cause of global climate change. The economic and environmental implications related to an increase in atmospheric greenhouse gas concentration have sparked interest in chemical capture and conversion of $CO_2$ to commodities that may otherwise be derived from crude oil sources. Despite its kinetic inactivity, $CO_2$ is an attractive $C_1$ feedstock as it is relatively non-toxic, renewable, and inexpensive. In this regard, an important transformation is the 100% atom economical reaction of $CO_2$ with epoxides to yield cyclic carbonates which have important applications as polar aprotic solvents, electrolytes in lithium-ion batteries, and monomers for production of polycarbonates. Although some catalytic methods have been reported for this transformation, the methods generally require high temperatures, high pressures, and/or long reaction times.

BACKGROUND

Thus, improved methods and systems for the synthesis of cyclic carbonates from $CO_2$ and epoxides are needed.

SUMMARY OF THE INVENTION

Described herein are inventive methods and systems relating to the formation of cyclic carbonates from $CO_2$ and epoxides.

In some embodiments, methods are provided comprising reacting a compound of Formula (I):

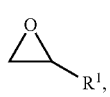
(I)

with $CO_2$ in the presence of a catalytic system to produce a compound of Formula (II):

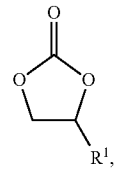
(II)

wherein $R^1$ is optionally substituted alkyl, optionally substituted cycloalkyl, optionally substituted heteroalkyl, optionally substituted heteroalkyl, optionally substituted aryl-alkyl, optionally substituted aryl-O-alkyl, optionally substituted aryl, optionally substituted heteroaryl, or optionally substituted alkenyl, and wherein the catalytic system comprises a catalyst comprising an electrophilic halogen.

In some embodiments, methods are provided comprising reacting a compound of Formula (I):

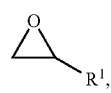
(I)

with $CO_2$ to produce a compound of Formula (II):

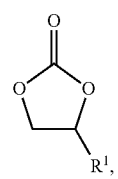
(II)

wherein $R^1$ is optionally substituted alkyl, optionally substituted cycloalkyl, optionally substituted heteroalkyl, optionally substituted heteroalkyl, optionally substituted aryl-alkyl, optionally substituted aryl-O-alkyl, optionally substituted aryl, optionally substituted heteroaryl, or optionally substituted alkenyl, wherein the reaction is a gas-liquid biphasic reaction.

Other advantages and novel features of the present invention will become apparent from the following detailed description of various non-limiting embodiments of the invention when considered in conjunction with the accompanying figures. Unless otherwise noted, all references cited herein are incorporated by reference in their entirety. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
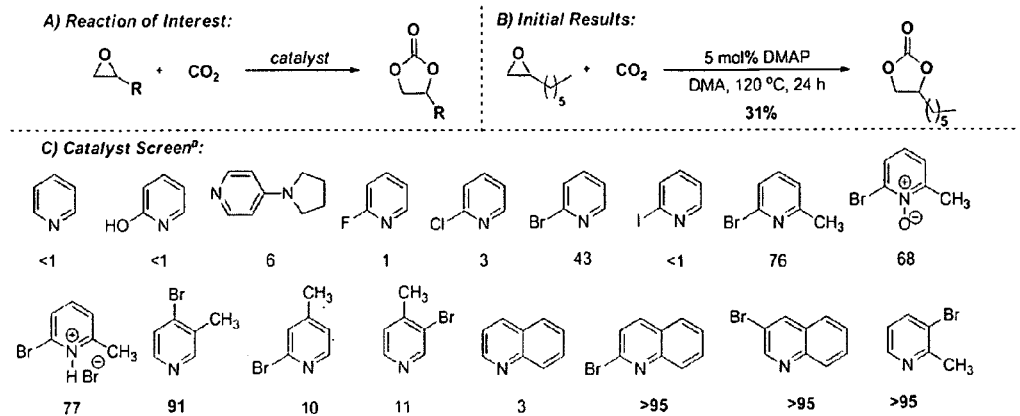
FIGS. 1A, 1B, 2, 4, and 5 show non-limiting examples of reactions of an epoxide and CO₂ to form a cyclic carbonate, according to some embodiments.
FIG. 1C shows non-limiting examples of exemplary catalysts, according to some embodiments.

Described herein are inventive methods and systems relating the synthesis of cyclic carbonates. In some cases, methods are provided for the synthesis of cyclic carbonates from $CO_2$ and epoxides. In some embodiments, the methods are carried out in the presence of a catalyst comprising an electrophilic halogen. In some embodiments, the methods are carried out in a flow reactor. The methods provided herein are capable of being carried out in short reaction times, with high yields, and/or with reduced costs as compared to current methods.

In some embodiments, methods are provided comprising reacting a compound of Formula (I):

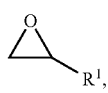

(I)

with CO₂ to produce a compound of Formula (II):

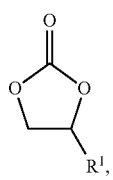

(II)

wherein $R^1$ is optionally substituted alkyl, optionally substituted cycloalkyl, optionally substituted heteroalkyl, optionally substituted heteroalkyl, optionally substituted aryl-alkyl, optionally substituted aryl-O-alkyl, optionally substituted aryl, optionally substituted heteroaryl, or optionally substituted alkenyl.

In some embodiments $R^1$ is substituted or unsubstituted alkyl. In some embodiments $R^1$ is —$(CH_2)_nCH_3$, wherein n is 0, 1, 2, 3, 4, 5, 6, 7, 8, 9, 10, or greater. In some embodiments, $R^1$ is —$(CH_2)_nOR^2$, wherein n is 0, 1, 2, 3, 4, 5, 6, 7, 8, 9, 10, or greater and $R^2$ is optionally substituted alkyl, optionally substituted heteroalkyl, optionally substituted heteroalkyl, optionally substituted aryl-alkyl, optionally substituted aryl-O-alkyl, optionally substituted aryl, optionally substituted heteroaryl, or optionally substituted alkenyl. In some cases, $R^2$ is substituted or unsubstituted aryl. In some embodiments, $R^1$ is —$(CH_2)_nR^3$, wherein n is 0, 1, 2, 3, 4, 5, 6, 7, 8, 9, 10, or greater and $R^3$ is halide, optionally substituted heteroalkyl, optionally substituted heteroalkyl, optionally substituted aryl-alkyl, optionally substituted aryl-O-alkyl, optionally substituted aryl, optionally substituted heteroaryl, or optionally substituted alkenyl. In some embodiments, $R^3$ is halide (e.g., F, Cl, Br, I). In some embodiments $R^3$ is substituted or unsubstituted aryl. In some embodiments, $R^3$ is substituted or unsubstituted aryl. In some embodiments, $R^3$ is Ph. In some embodiments, $R^1$ is —$(CH_2)_nCH=CH_2$, wherein n is 0, 1, 2, 3, 4, 5, 6, 7, 8, 9, 10, or greater. In some embodiments, a compound of Formula (I) and/or Formula (II) is as provided in Table 3.

In some embodiments, a chiral cyclic carbonate may be prepared (e.g., see Example 3). For example, in some embodiments, a cyclic carbonate may be prepared having an enantiomeric excess greater than about 50%, greater than about 60%, greater than about 70%, greater than about 80%, greater than about 90%, greater than about 95%, greater than about 98%, or greater than about 99%. In some embodiments, the cyclic carbonate may be a racemic mixture. In some embodiments, the stereochemistry of the epoxide may be retained during the formation of the cyclic carbonate. In other embodiments, the stereochemistry of the epoxide may be inverted during the formation of the cyclic carbonate.

In some embodiments, the reacting may be carried out in the presence of a catalytic system. The catalytic system may comprise one or more catalysts (e.g., one catalyst, two catalysts, three catalysts). As will be known to those or ordinary skill in the art, a catalytic system may be present to help increase the rate of a reaction and/or to improve the selectivity of a reaction. In some embodiments, the presence of a catalytic system may aid in increasing the rate of reaction from the starting materials to the cyclic carbonate. In some embodiments, the catalytic system comprises a catalyst comprises an electrophilic halogen. In certain embodiments, the catalytic system comprises a catalyst comprising an electrophilic bromine. In certain embodiments, the catalytic system comprises a catalyst comprising an electrophilic chlorine. In certain embodiments, the catalytic system comprises a catalyst comprising an electrophilic iodine. In some embodiments, the catalytic system comprises an oxidant and a catalyst comprising an electrophilic halogen. In some embodiments, the catalytic system comprises a catalyst comprising an electrophilic halogen and a catalyst comprising a nucleophilic nitrogen atom (e.g., comprising an amide). In some embodiments, the catalytic system comprises a catalyst comprising an electrophilic halogen, an oxidant, and a catalyst comprising a nucleophilic nitrogen atom. Without wishing to be bound by theory, the nucleophilic halogen may activate the epoxide (e.g., see proposed mechanism in FIG. 7).

In some embodiments, the catalytic system comprises a catalyst comprising an electrophilic halogen. The term "electrophilic halogen" as used herein is given its ordinary meaning in the art and refers to an electron-deficient halogen (e.g., an electron-deficient bromine, chlorine, or iodine), generally positively charged (e.g., $Br^+$), but also possibly a halogen radical (Br.). In some embodiments, a catalyst comprising an electrophilic bromine provides a source of $Br^+$ ions. In some embodiments, a catalyst comprising an electrophilic chlorine provides a source of $Cl^+$ ions. In some embodiments, a catalyst comprising an electrophilic iodine provides a source of $I^+$ ions. Those of ordinary skill in the art will be aware of suitable catalysts comprising an electrophilic halogen. Non-limiting examples of catalysts comprising an electrophilic bromine include N-bromosuccinimide (NBS), 2,4,4,6-tetrabromocyclohexa-2,5-dienone (TBCO), $Br_2$, $[Si(Et)_2Br]^+[SbCl_5Br]^-$, $Br(collidine)_2ClO_4$, and $Br(collidine)_2PF_6$. In some embodiments, the catalyst comprising an electrophilic bromine is NBS. Non-limiting examples of catalysts comprising an electrophilic chlorine include N-chlorosuccinimide (NCS), $Cl_2$, chloramine-T, and hexachloroquinone. Non-limiting examples of catalysts comprising an electrophilic iodine include N-iodosuccinimide (NIS), $I_2$, KI/potassium peroxymonosulfate (e.g., Oxone®), and ICl.

In some embodiments, the catalytic system comprises a catalyst comprising a nucleophilic nitrogen and/or oxygen atom (e.g., a compound comprising an electron-rich nitrogen and/or oxygen atom). In some embodiments, catalyst comprising a nucleophilic nitrogen atom and/or oxygen atom comprises an amide, a urea (e.g., tetramethylurea), an amidine (e.g., 1,8-diazabicycloundec-7-ene ("DBU")), a pyridine, (e.g., pyridine), or an imide (e.g., N-methylsuccinimide). In some embodiments, catalyst comprising a nucleophilic nitrogen atom and/or oxygen atom comprises an amide. The term "amide" as used herein is given its ordinary meaning in the art and refers to a compound having the structure R'C(O)N(R')$_2$, wherein each R' is independently hydrogen, optionally substituted alkyl, optionally substituted alkenyl, optionally substituted alkynyl, optionally substituted aralkyl, optionally substituted cycloalkyl, optionally substituted heterocycloalkyl, optionally substituted aryl, or optionally substituted heteroaryl, or optionally, any two R' may be joined together to form a ring. In some embodiments, each R' are independently hydrogen or optionally substituted aryl. In some embodiments, the catalyst comprising the nucleophilic nitrogen atom may also function as a solvent. For example, in some embodiments, the compound comprising an amide comprises dimethylformamide (DMF), dimethylacetamide (DMA), N-methyl-2-pyrrolidone (NMP), or combinations thereof.

In some embodiments, the catalytic system comprises an oxidant. The term "oxidant" as used herein is given its ordinary meaning in the art and refers to a chemical compound that readily transfers oxygen atoms and oxidize other compounds, or a substance that gains electrons in a redox chemical reaction. Non-limiting examples of oxidants include benzoyl peroxide (BPO), KI/potassium peroxymonosulfate (e.g., Oxone®), O$_2$, and cobaltacene (Cp$_2$Co$^+$).

A catalyst (e.g., as part of a catalytic system) may be provided in any suitable amount. In some embodiments, a catalyst is provided in about 1 mol %, about 2 mol %, about 3 mol %, about 4 mol %, about 5 mol %, about 6 mol %, about 7 mol %, about 8 mol %, about 9 mol %, about 10 mol %, or greater, versus the compound of Formula (I). In some embodiments, a catalyst is provided in an amount between about 1 mol % and about 10 mol %, or about 5 mol % and about 10 mol %, or about 5 mol % and about 15 mol %, versus the compound of Formula (I). In other embodiments, the catalyst is provided in less than 1 mol % or greater than 15 mol %. It should be understood, in embodiments wherein a catalyst is also acting as a solvent (e.g., DMF, DMA, NMP, etc.), the amounts listed above will not apply.

The CO$_2$ may be provided by any suitable source. In some embodiments, CO$_2$ source is from fossil fuel combustion. The CO$_2$ may be provided at any suitable pressure. In some embodiments, the CO$_2$ is provided at ambient pressure. In other embodiments, the CO$_2$ is provided at elevated temperatures.

In some embodiments, the reaction is carried out at high temperatures. The use of high temperatures may allow for the reaction to be carried out in shorter periods of time as compared to at lower temperatures. In some embodiments, the reaction may be carried out at a temperature between about 50° C. and about 150° C. In some cases, the reaction may be carried out at a temperature of between about 50° C. and about 140° C., about 60° C. and about 130° C., about 70° C. and about 120° C., about 80° C. and about 120° C., or about 80° C. and about 100° C. In some embodiments, the reaction may be carried out at a temperature of about 50° C., about 60° C., about 70° C., about 80° C., about 90° C., about 100° C., about 110° C., about 120° C., or about 130° C. In some cases, the reaction may be carried out at a temperature below about 130° C., below about 120° C., below about 110° C., below about 100° C., below about 90° C., or below about 80° C. In other embodiments, the reaction may be carried out at lower than 50° C. or higher than 150° C.

In some embodiments, the reaction may be carried out in an inert atmosphere. For example, the reactions may be carried out in or under an inert nitrogen or argon atmosphere (e.g., using standard Schlenk techniques and/or in an inert-atmosphere glovebox).

The methods described herein may be carried out in any suitable solvent, including, but are not limited to, non-halogenated hydrocarbon solvents (e.g., pentane, hexane, heptane, cyclohexane), halogenated hydrocarbon solvents (e.g., dichloromethane, chloroform, fluorobenzene, trifluoromethylbenzene), aromatic hydrocarbon solvents (e.g., toluene, benzene, xylene), ester solvents (e.g., ethyl acetate), ether solvents (e.g., tetrahydrofuran, dioxane, diethyl ether, dimethoxyethane.), and alcohol solvents (e.g., ethanol, methanol, propanol, isopropanol, tert-butanol). Non-limiting examples of solvents useful include acetone, acetic acid, formic acid, dimethyl sulfoxide, dimethyl formamide, acetonitrile, p-cresol, glycol, petroleum ether, carbon tetrachloride, hexamethyl-phosphoric triamide, triethylamine, picoline, and pyridine. In some embodiments, the solvent is DMP, DMA, NMP, or combinations thereof. In some embodiments, the solvent is DMP. In some embodiments, the solvent is DMA. Other solvents will be known to those of ordinary skill in the art.

In some embodiments, the solvent may also act as a catalyst. For example, in some embodiments, the solvent may comprise a nucleophilic nitrogen atom, and the solvent may function as a catalyst in the reacting. Non-limiting examples of solvents comprising a nucleophilic nitrogen atom which may also function as a catalyst include DMP, DMA, and NMP.

The reaction may be carried out for any suitable period of time. In some cases, the reaction is carried out until the reaction is about 50%, about 60%, about 70%, about 80%, about 90%, about 93%, about 95%, about 96%, about 97%, about 98%, about 99%, about 99.5%, or greater, complete. That is, the reaction is carried out for a period of time until a selected percent of the starting material has been converted into a product. In some cases, the reaction is greater than about 50%, about 60%, about 70%, about 80%, about 90%, about 93%, about 95%, about 96%, about 97%, about 98%, about 99%, about 99.5%, or greater, complete in a period of time of less than about 24 hours, less than about 12 hours, less than about 8 hours, less than about 6 hours, less than about 5 hours, less than about 4 hours, less than about 3 hours, less than about 2 hours, less that about 1 hour, less than about 50 minutes, less than about 40 minutes, less than about 30 minutes, or less.

In some embodiments, a method for forming a cyclic carbonate is conducted in a flow reactor. Flow reactors will be known to those of ordinary skill in the art. In some embodiments, the reaction carried out is a gas-liquid biphasic reaction. In some embodiments, the reaction is carried out in the absence of a solid support. In some embodiments, the catalyst(s) are not associated with a solid support (e.g., the catalysts are in solution).

Flow reactors may be provided in various configurations and may be equipped with a number of components to utilize methods described herein. Non-limiting components of a flow reactor include inlet(s) (e.g., for reactants, solvents, gases (e.g., CO$_2$) etc.), reaction tube and/or chamber (e.g., where the reaction occurs), outlet(s), pressure controller(s)

Figure 2:
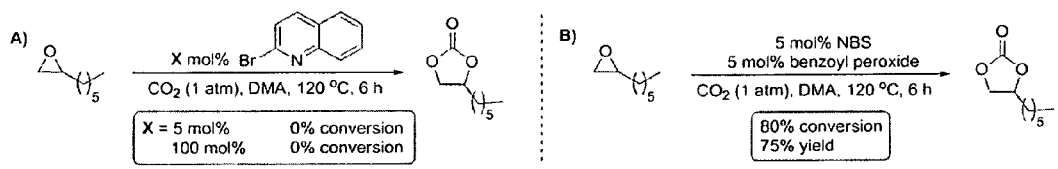
Figure 6:
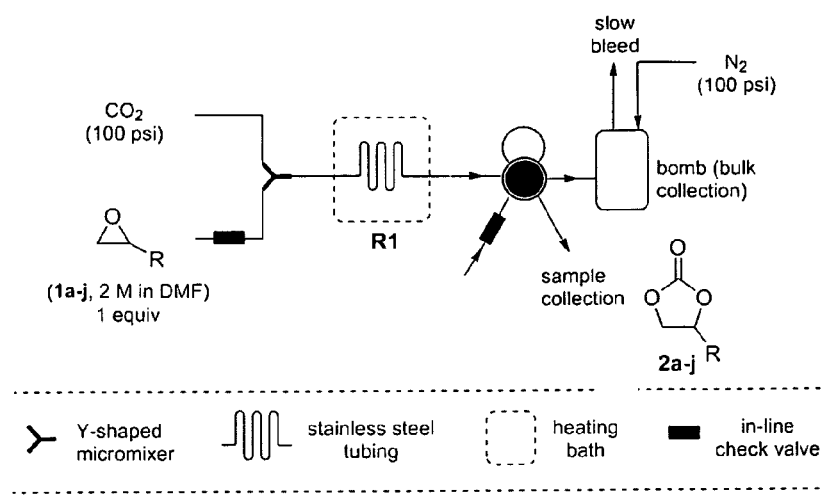

(e.g., back pressure regulators), and temperature control device(s) (e.g., heating device(s) and/or cooling device(s)). Non-limiting examples of flow reactor are shown in FIGS. 2 and 6 and are described in more detail herein.

In some embodiments, a method of the present invention comprises providing $CO_2$ and an epoxide (e.g., a compound of Formula (I)) to one or more inlets of a flow reactor. The reaction components may be flowed through the flow reactor (e.g., in the reaction tube and/or chamber) for a suitable period of time, during which time, a cyclic carbonate (e.g., a compound of Formula (II)) forms. Following the selected amount of time in the flow reactor, the reaction products, including side products and reagents, may be collected at one or more outlets of the flow reactor.

In some embodiments, the various conditions of the flow reactor may be selected such that the cyclic carbonate (e.g., a compound of Formula (II)) is formed in short reaction times and/or in good yields. Those of ordinary skill in the art will be able to use the guidelines described herein to select appropriate reaction conditions for the selected reactant without undo experimentations. Non-limiting parameters which may be varied include the solvent selection, the temperature of reaction, the nature of the substituents on the reactant, the presence, or absence of a catalyst, and/or the reaction time, variations of which are now described in detail.

A non-limiting example of a flow reactor method of the present invention is as follows. The flow reactor may comprise one or more inlets. In the one or more inlets a compound of Formula (I), and optionally one or more catalysts, may be provided in a solvent (e.g., a solvent such as DMF, DMA, NMP, which may also function as a catalyst). In addition, the flow reaction may comprise an inlet for the $CO_2$. The inlets may be connected to the reaction tube and/or chamber. The reaction tube and/or chamber may be associated with one or more temperature control devices such that the temperature in the reaction chamber/tube can be controlled. In some cases, the reaction chamber/tube comprising a metal tubing which is immersed in a heating bath (e.g., oil bath) which is maintained at the desired temperature for the reaction. The reactants may be flowed through the reaction chamber by application or a positive pressure at the inlet (e.g., continued flow of the reactants and/or solvents) and/or a negative pressure at the outlet (e.g., caused by vacuum). While in the reaction chamber/tube, the epoxide (e.g., a compound of Formula (I)) and the $CO_2$ source may react (e.g., during flow of the solvent through the flow reactor) to form a cyclic carbonate (e.g., a compound of Formula (II)). The system may be designed such that the reactants are contained in the flow chamber/tube for the appropriate period of time such that the reaction proceeds to almost completion. The amount of time required will depend on the reaction conditions (e.g., temperature, reactants, solvents, etc.). The residence time in the flow chamber may be controlled using techniques known to those of ordinary skill in the art, including, but not limited to, altering the speed of the flow of the reactant through the flow chamber and/or the length of the reaction tube/chamber, etc. The system may also comprise one or more pressure regulators (e.g., backflow pressure regulator). The reaction mixture may then be collected (e.g., via an outlet) and the product isolated and/or purified, e.g., using techniques known to those of ordinary skill in the art.

DEFINITIONS

For convenience, certain terms employed in the specification, examples, and appended claims are listed here.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry," Thomas Sorrell, University Science Books, Sausalito: 1999, the entire contents of which are incorporated herein by reference. As used herein, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$—C for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like, each optionally substituted.

The terms "alkenyl" and "alkynyl" refer to unsaturated aliphatic groups analogous to the alkyl groups described above, but containing at least one double or triple bond respectively. Alkenyl and alkynyl groups may be analogous in length and possible substitutions to the alkyls described above, but contain at least one double or triple bond, respectively. The "heteroalkenyl" and "heteroalkynyl" refer to alkenyl and alkynyl groups as described herein in which one or more atoms is a heteroatom (e.g., oxygen, nitrogen, sulfur, and the like).

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$ R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

"Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc., each optionally substituted.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl) aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound. It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O) R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted heteroalkyl" must still comprise the heteroalkyl moiety and can not be modified by substitution, in this definition, to become, e.g., an alkyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

These and other aspects of the present invention will be further appreciated upon consideration of the following Examples, which are intended to illustrate certain particular embodiments of the invention but are not intended to limit its scope, as defined by the claims.

Example 1

Anthropogenic carbon dioxide ($CO_2$) from fossil-fuel combustion is cited as the leading cause of global climate change. The economic and environmental implications related to an increase in atmospheric greenhouse gas concentration have sparked interest in chemical capture and conversion of $CO_2$ to commodities that may otherwise be derived from crude oil sources. Despite its kinetic inactivity, $CO_2$ is an attractive $C_1$ feedstock as it is relatively non-toxic, renewable, and inexpensive. In this regard, an important transformation is the 100% atom economical reaction of $CO_2$ with epoxides to yield cyclic carbonates (FIG. 1A) which have important applications as polar aprotic solvents, electrolytes in lithium-ion batteries, and monomers for production of polycarbonates. Although some catalytic methods have been reported for this transformation, the methods generally require high temperatures and/or pressures, and long reaction times.

In FIG. 1: (A) Reaction of an epoxide with $CO_2$ to produce a cyclic carbonate. (B) Using 5 mol % of DMAP as a catalyst afforded 31% of the corresponding cyclic carbonate product. (C) Non-limiting catalyst employed for the reaction. [a] Conversion is indicated below each structure. Conversion was determined from GC analysis.

Recent research has focused on the direct conversion of $CO_2$ from the waste streams (flue gas) of coal-fired power plants into useful chemical compounds, including cyclic carbonates. An ideal process would be use of the flue gas directly in a continuous flow reactor (carbon capture and conversion). Continuous flow processes have several key advantages which may allow for the large scale production of useful chemicals from $CO_2$. These include, but are not limited to: (1) the high surface area-to-volume ratios of small reactors results in excellent heat transfer, allowing for fine control of reaction temperature, (2) the contact area between the liquid and gas interfaces is significantly higher with slug flow compared to batch reactors, and (3) continuous flow reactors have high safety profiles as only a small portion of the reactor is subjected to high temperatures and/or pressures.

In FIG. 2 (A) A long induction period rendered the reaction unsuitable for continuous flow conditions. (B) A novel organocatalytic system showed no induction period in a traditional batch reactor.

A novel method for the capture of $CO_2$ and its transformation to cyclic carbonates was investigated, e.g., using standard batch conditions. It was found that 1,2-epoxyoctane, $CO_2$ (balloon pressure), and a catalytic quantity of 4-(dimethylamino)pyridine (DMAP) afforded the corresponding cyclic carbonate in 31% yield after 24 hours at 120° C. (FIG. 1B). Other catalysts of similar structure were also evaluated and selected results are shown in FIG. 1C. 2-Bromoquinoline was selected as an exemplary catalyst for further reaction optimization in both a batch reactor and in the continuous flow apparatus.

Experimentation revealed challenges associated with employing 2-bromoquinoline as the catalyst for continuous flow conditions due to an induction period of approximately 8-10 h (FIG. 2A); even with 20 times the concentration of the catalyst, no reaction was observed after 6 h. These observations led to the development of a new dual catalyst system comprised of N-bromosuccinimide (NBS) and benzoyl peroxide that is suitable for use in a flow reactor. When 5 mol % of NBS and 5 mol % of benzoyl peroxide were added to the reaction mixture under the conditions shown in FIG. 2B, 80% epoxide conversion and 75% yield of cyclic carbonate was observed.

Figure 3:
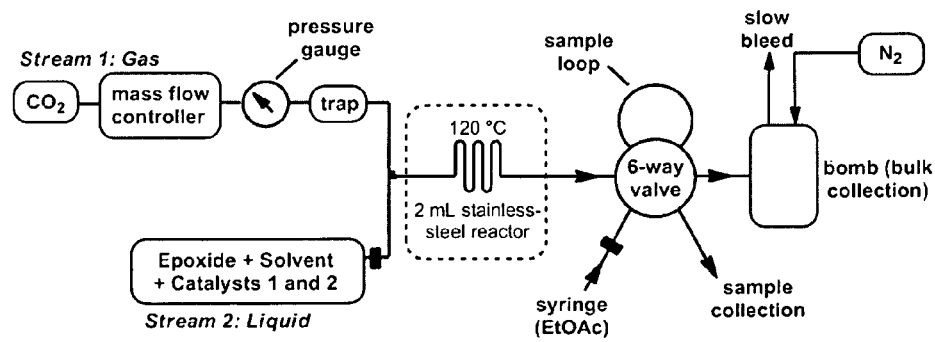
FIGS. 3, 6, 8A, and 8B illustrate non-limiting examples of flow reactors, according to some embodiments.

In FIG. 3: Illustrative design of a non-limiting liquid-gas continuous flow apparatus for the conversion of epoxides and $CO_2$ to cyclic carbonates To test these conditions using continuous flow, a reactor was designed and built to allow efficient mixing of gas and liquid at pressure (FIG. 3). The reactor was built on the bench top using commonly available materials and devices. A feature of this reactor design was the 6-way valve that allows for sampling of the reaction without releasing pressure from the system. Using the organocatalytic system in the flow reactor, several parameters (amount of catalyst, concentration, solvent, and residence time) were rapidly optimized. It was discovered that the residence time could be reduced from 40 min to 20 min by increasing the concentration of epoxide from 0.44 to 2 M (FIG. 4A; all entries). Next, a series of epoxides were investigated (FIG. 4B). The conditions proved efficient in the conversion of a variety of epoxides (e.g., terminal epoxides) to the corresponding cyclic carbonates after only 30 minutes. The conditions described may be employed for a variety of reagents, including terminal epoxides. In some cases, certain reagents proved more challenging (e.g., trans-stilbene oxide, 1,2-epoxy-2-methypropane, cyclohexene oxide, and 2-methyl-2-vinyloxirane).

Figure 4:
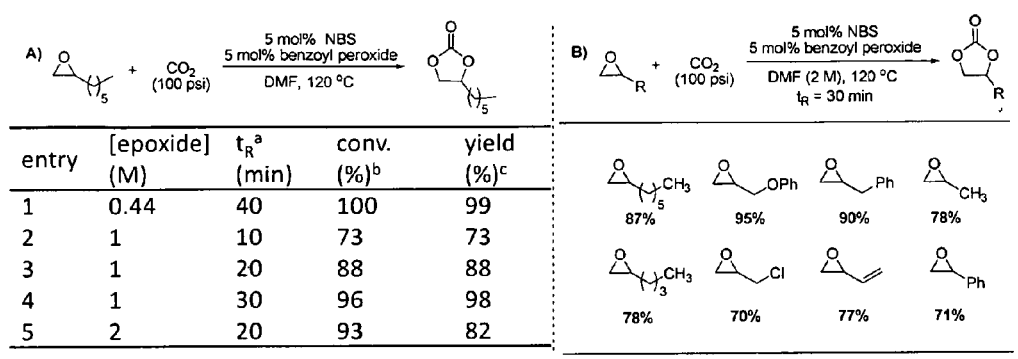

In FIG. 4: (A) Optimization of continuous flow conditions, according to some embodiments. (B) Non-limiting examples of terminal epoxides. [a] Sampling for each reaction occurred after 3-4 residence times ($t_R$'s) to ensure steady-state conditions. [b] Conversion determined by GC analysis using an internal standard. [c] Yield determined by $^1$H NMR analysis using an external standard.

Kinetics experiments can provide some are information regarding reaction mechanism. In some cases, the reaction is first order in NBS, zero order in benzoyl peroxide, and zero order in $CO_2$.

In summary, a laboratory scale flow system was developed to enable the continuous transformation of $CO_2$ into useful chemicals. The novel organocatalytic system developed was suitable under continuous flow conditions and was efficient in converting epoxides (e.g., terminal epoxides) to the corresponding cyclic carbonate in about 30 minutes. The design of the flow reactor may be extended to larger systems which can allow for the use of $CO_2$ from a flue gas stream for chemical transformation into useful and/or commodity chemicals.

Example 2

This example describes a continuous method for the formation of cyclic carbonates from epoxides and carbon dioxide ($CO_2$) is described. The catalysts used are inexpensive, commercially available organic compounds and are effective in converting the reagents to the products in a residence time ($t_R$) of 30 min. The cyclic carbonate products are obtained in good to excellent yield (51-92%). Based on a series of kinetics experiments, a reaction mechanism that involves a novel mode of epoxide activation by electrophilic bromine is discussed.

Figure 5:
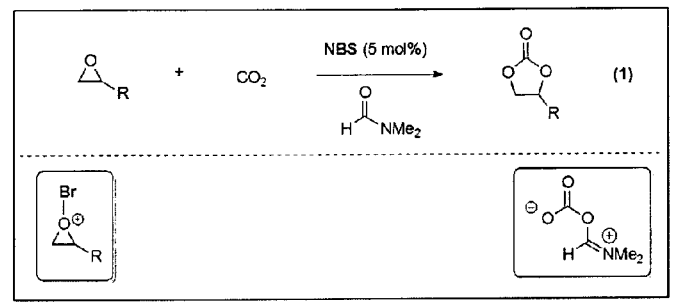

Introduction:

Carbon dioxide is an attractive $C_1$ feedstock as it is renewable, inexpensive, and can replace commonly used toxic $C_1$ building blocks, such as phosgene. In this regard, an important transformation is the atom economical reaction of $CO_2$ with epoxides to yield cyclic carbonates (FIG. 5, eq 1), which have important applications as polar aprotic solvents, electrolytes in lithium-ion batteries, and are useful monomers for the production of polycarbonates. However, a central challenge common to all transformations employing $CO_2$ is overcoming its kinetic and thermodynamic stability.

In recent years, many homogeneous and heterogeneous catalytic systems have been developed to carry out this transformation. Examples of these catalytic systems include, but are not limited to, metal-salen complexes, metal-oxides, organic bases or ammonium and phosphonium salts, N-heterocyclic carbenes, alkali metal salts, and ionic liquids. Often these systems suffer drawbacks associated with high catalyst loading, long reaction times, expensive and/or metal-based catalyst systems, the necessity of high pressures and/or temperatures, and/or low efficiency. This example describes a catalytic system comprising N-bromosuccinimide (NBS) and benzoyl peroxide (BPO) in DMF for the efficient and continuous conversion of epoxides and $CO_2$ to cyclic carbonates. A possible mechanism comprises an electrophilic bromine cation activating the epoxide. These studies further support the nucleophilic activation of $CO_2$ by DMF (solvent KIE). Additional experimental details relating to the results provided in this example are provided in Example 3.

Results and Discussion:

Continuous flow methods have emerged as enabling technologies for chemical transformations, particularly for gas-liquid biphasic reactions. In this example the enhanced mass transport between the two phases in a continuous flow apparatus may enhance the efficiency and throughput of $CO_2$ capture and conversion relative to existing literature reports. A continuous flow apparatus from commercially available components was constructed (FIG. 6). The experimental procedure is summarized as follows: After the system was brought to the appropriate pressure (100 psi of $CO_2$) and temperature (120° C.), a solution of epoxide (1a-j) and catalyst in DMF was introduced by syringe pump. The $CO_2$ stream was metered into the system using a mass flow controller. The gas and liquid streams met at a Y-mixer, and a 1:1 (v:v) liquid/gas slug flow stream was observed at the out port. The reaction occurred at elevated temperature in standard stainless steel tubing (R1; 0.030" i.d.). Nitrogen ($N_2$) was employed for back pressure and a slow bleed was necessary to regulate the overall pressure of the system. After steady state was achieved (~4×$t_R$), the final eluent stream was sampled using a 6-way valve.

In the initial studies of the reaction of $CO_2$ with epoxides (batch), a catalyst system that a) employed inexpensive and readily available compounds, b) did not necessitate high $CO_2$ pressures, and c) would be amenable to continuous flow production. During an evaluation of several classes of potential promoters, N-bromosuccinimide (NBS) emerged as an effective catalyst for the formation of cyclic carbonates from the corresponding epoxide and $CO_2$. For example, in the presence of 5 mol % of NBS in DMA, 75% conversion of 1,2-epoxyoctane (1a) to cyclic carbonate 2a was observed after 6 h at 120° C. (Table 1, entry 1). Achieving a reasonable reaction time in flow (~45 min) was a significant challenge for this process. Essentially conversion of 1,2-epoxyoctane (1a) was observed with 5 mol % of NBS at 80° C., even with extending the $t_R$ to 45 min (entry 2). Increasing the temperature to 120° C. gave only 24% conversion (entry 3). An important difference between the batch and flow experiments may be the role of adventitious oxygen in the former. As such, the addition of an oxidant, benzoyl peroxide (BPO), to the continuous process resulted in 100% epoxide conversion under otherwise identical conditions (entry 4). Full epoxide conversion was also observed with decreased catalyst loading (5 mol %, entry 5).

In order to increase efficiency and volumetric throughput, decreased $t_R$ and minimized the amount of solvent was sought. Increasing the concentration of the epoxide in DMF to 1.0 M, and decreasing the residence time to 10 min led to 73% conversion and identical yield (Table 2, entry 2).

TABLE 1

Initial experiments using the continuous flow apparatus.

| entry | catalyst | T (° C.) | time | [1a]₀ (M) | conversion (%)[c] |
|---|---|---|---|---|---|
| 1[a] | 5% NBS | 120 | 6 h | 0.44 | 75 |
| 2[b] | 5% NBS | 80 | 45 min | 1.0 | 0 |
| 3[b] | 10% NBS | 120 | 45 min | 1.0 | 24 |
| 4[b] | 10% NBS + 10% BPO | 120 | 45 min | 1.0 | 100 |
| 5[b] | 5% NBS + 5% BPO | 120 | 45 min | 0.44 | 100 |

[a]Batch reaction (atmospheric $CO_2$ pressure).
[b]Flow experiment (100 psi $CO_2$ pressure).
[c]Conversion determined by GC analysis using naphthalene as an internal standard.
NBS = N-bromosuccinimide.
BPO = benzoyl peroxide.

Increasing $t_R$ to 30 min led to nearly full conversion (entry 4), and a further increase of epoxide concentration (2.0 M) and a decrease of $t_R$ (20 min) gave a slight reduction in both conversion and yield (entry 5). Any additional increase in epoxide concentration was detrimental to reactivity. The conditions of 5 mol % of both NBS and benzoyl peroxide, an epoxide concentration of 2.0 M in DMF, and a $t_R$ of 30 min (entry 6) were desirable in some case (herein after "Conditions A").

TABLE 2

Optimization of continuous flow cyclic carbonate synthesis.

[Reaction scheme: 1a + CO$_2$ (100 psi) → 2a, with 5 mol % NBS, 5 mol % BPO, DMF, 120° C.]

| entry | $[1a]_0$ (M) | $t_R$ (min)$^a$ | conv (%)$^b$ | yield (%)$^c$ |
|---|---|---|---|---|
| 1 | 0.44 | 45 | 100 | 99 |
| 2 | 1 | 10 | 73 | 73 |
| 3 | 1 | 20 | 88 | 88 |
| 4 | 1 | 30 | 96 | 98 |
| 5 | 2 | 20 | 93 | 82 |
| 6 | 2 | 30 | 96 | 87 |

$^a$Each reaction was sampled after 4 × $t_R$ to ensure steady-state conditions.
$^b$Conversion was determined by GC analysis using naphthalene as an internal standard.
$^c$Yield was determined by $^1$H NMR using trichloroethylene as an external standard.

Using the Conditions A in the continuous flow apparatus (Table 2, entry 6), epoxides bearing different functional groups (Table 3) were investigated. All terminal epoxides were converted to the corresponding cyclic carbonates in good to excellent yields with no observable byproduct formation (entries 1-7). Propylene oxide (1d), a low boiling epoxide that can be difficult to handle, underwent smooth conversion to propylene carbonate (2d) in 81% yield (entry 4). Alkene-containing epoxides (1h-j) formed cyclic carbonate products in 52%, 58%, and 51% yield (entries 8-10, respectively). The pendant alkene may interfere with the active catalyst in the reaction mixture (vide infra in some embodiments). Overall, the utility of the continuous flow reactor was demonstrated by the rapid synthesis of a variety of cyclic carbonates with no observable byproducts.

Mechanistic Considerations:

The reaction conditions discovered stand in stark contrast to those previously reported for this transformation; most of the components employed herein would generally be considered electrophilic in nature. That is, it was not clear as to how two electrophilic catalysts (NBS and BPO) were mediating the coupling of two electrophiles (epoxide and CO$_2$). In order to gain mechanistic insight into this apparent paradox, kinetic parameters of the coupling of 1,2-epoxyoctane (1a) and CO$_2$ catalyzed by NBS and benzoyl peroxide in DMF were determined.

TABLE 3

Synthesis of cyclic carbonates from epoxides and CO$_2$.$^a$

| entry | epoxide | product | yield (%)$^b$ |
|---|---|---|---|
| 1 | 1a | 2a | 87 (96)$^c$ |
| 2 | 1b | 2b | 86 (87)$^c$ |
| 3 | 1c | 2c | 90 (93)$^c$ |
| 4 | 1d | 2d | 81 |
| 5 | 1e | 2e | 83 |
| 6 | 1f | 2f | 78 |
| 7 | 1g | 2g | 72 |

TABLE 3-continued

Synthesis of cyclic carbonates from epoxides and $CO_2$.[a]

| entry | epoxide | product | yield (%)[b] |
|---|---|---|---|
| 8 | 1h | 2h | 52 |
| 9 | 1i | 2i | 58 |
| 10 | 1j | 2j | 51 (42)[d] |

[a] See Table 2, entry 6 for experimental conditions.

[b] Yield determined by $^1$H NMR using trichloroethylene as an external standard.

[c] Conversion (in parentheses) determined by GC analysis using naphthalene as an internal standard.

[d] Conversion (in parentheses) determined by $^1$H NMR.

The rate of the reaction displayed a first-order dependence on both the epoxide and NBS concentrations, while a zeroth-order dependence was observed for the concentration of benzoyl peroxide. The reaction rate was independent of $CO_2$ pressure.

Taken together, these experiments suggest the following rate expression:

$$\text{rate} = k_{obs}[\text{epoxide}]^1[NBS]^1[BPO]^0[CO_2]^0 \quad (2)$$
$$= k_{obs}[\text{epoxide}][NBS]$$

Next, a solvent study revealed that DMF, DMA, and NMP are involved in the reaction, suggesting that the solvent may also be a direct promoter of the reaction. The reaction of amides with NBS is known. Participation of DMF in the reaction mechanism was verified by carrying out a solvent kinetic isotope effect (KIE) experiment. The relative rate of the reaction in DMF and DMF-$d_7$ (eq 3, Scheme 1) was determined to be 1.3, suggesting a secondary KIE, such as a change of hybridization within DMF.

Scheme 1:

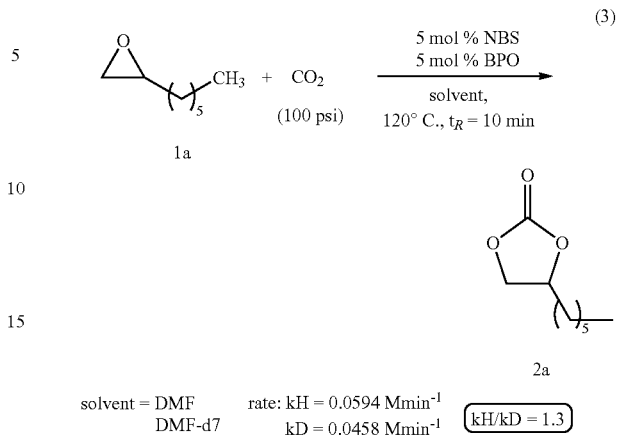

Figure 7:
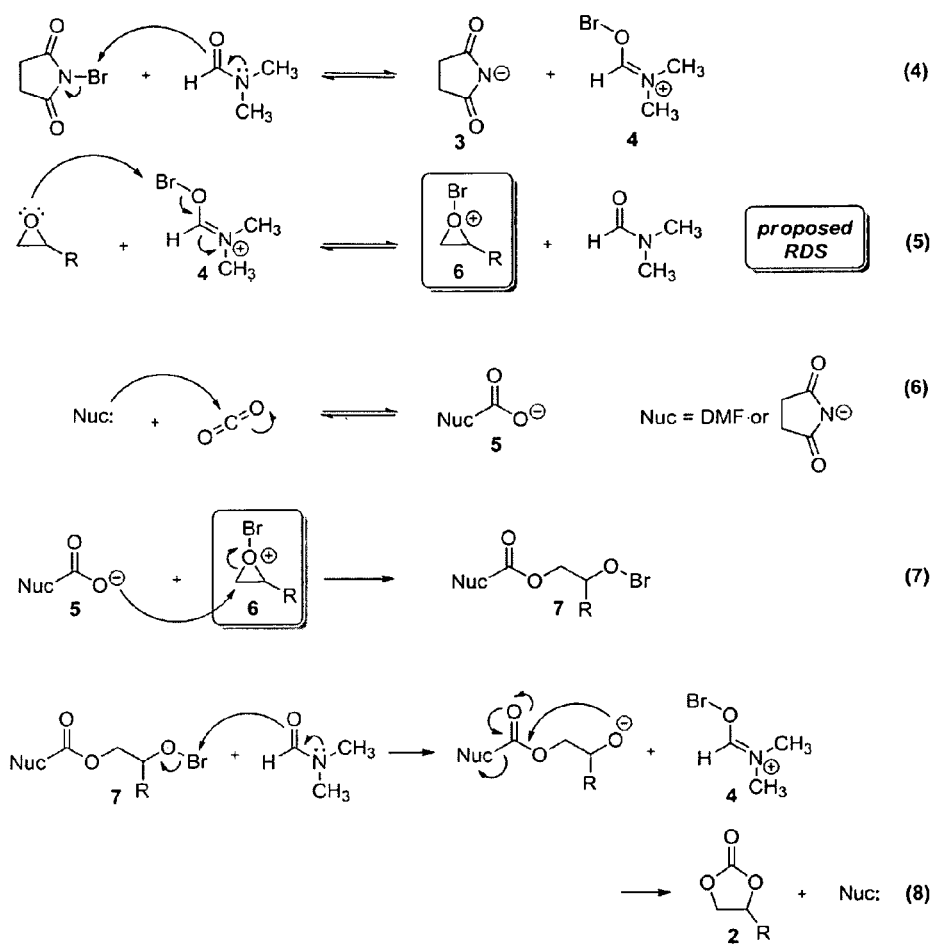
FIG. 7 illustrates a proposed mechanism for reaction, according to some embodiment.

On the basis of these results, the a mechanism may involve a bromo-oxonium species (6), formed after an initial activation of NBS by DMF. This mechanism is consistent with the solvent KIE and first-order dependence of reaction rate upon [NBS] and [epoxide] (FIG. 7). Bromine is known to react with other oxygen-containing compounds, such as ethers; Dioxane forms an isolable complex with elemental bromine. With sufficient nucleophilic activation, $CO_2$ can react with 6 to give compound 7 (eq 7). Enantiomerically pure (S)-1b was converted to enantiomerically pure (R)-2b (retention of configuration), consistent with epoxide opening at the less hindered (terminal) position. Enantiomerically pure (R)-styrene oxide ((R)-1g), on the other hand, was transformed to (R)-2g of 76% ee, presumably due to increased stabilization of positive charge at the 2-position by the Ph group. An 88:12 regioselectivity of epoxide opening (with complete inversion of configuration of the minor regioisomer) would be one scenario that would explain this result. It is also possible that the minor enantiomer is the result of an $S_N1$-like mechanism, followed by stereorandom attack of an activated $CO_2$ nucleophile (e.g., 5, FIG. 7). At the extreme, the regioselectivity in this case would be 76:24 in order to account for the observed ee of the product (76% (R) from opening at terminal position and 12% each of (S) and (R) from opening at the internal position with racemization. Intermediate scenarios in which $S_N2$ and $S_N1$ pathways both contribute are of course also possible. See the methods for details. There are a number of species in the reaction mixture that could fulfill this role. Possibilities include the succinimide anion (eq 6) or a molecule of DMF After epoxide opening, the O—Br bond may be broken by DMF, regenerating the DMF-Br$^+$ catalyst (4, eq 8). The alkoxide anion thus liberated can then cyclize to form the cyclic carbonate product and regenerate the nucleophilic catalyst. The reaction rate is zeroth-order in BPO. In FIG. 7: A proposed mechanism of the reaction.

BPO may oxidize any adventitious bromide ions to $Br_2$, thus maintaining a maximum concentration of active catalyst in solution (Br$^+$ or DMF-Br$^+$ complex). With 5 mol % $Br_2$, 1,2-epoxyoctane (1a) was converted to cyclic carbonate 2a as efficiently as with 5 mol % NBS and 5 mol % BPO.

Conclusion:

An efficient method has been developed for the high yielding continuous synthesis of cyclic carbonates from $CO_2$ and epoxides. A continuous flow apparatus for gas/liquid reactions can greatly enhance the efficiency of the transformation relative to a traditional batch reactor was demonstrated. The catalysts used are commercially available and inexpensive. A series of kinetics experiments uncovered mode of epoxide activation by electrophilic bromine.

Example 3

The following example provides supporting details for the experiments conducted in Example 2.

General Experimental Information:

All reactions sensitive to air or moisture were carried out in flame-dried glassware under an atmosphere of argon. Volumetric flasks were oven-dried and cooled in a desiccator prior to use. Anhydrous N,N-dimethylformamide (DMF) and N,N-dimethylacetamide (DMA) were purchased from Sigma-Aldrich and used without any further purification. 1,2-Epoxyoctane (1a) was distilled from calcium hydride prior to use. All other commercial reagents or materials were used as received without purification: 1,2-epoxy-3-phenoxypropane (1b), (2,3-epoxypropyl)benzene (1c), propylene oxide (1d), (1,2-epoxyhexane (1e), epichlorohydrin (1f), styrene oxide (1g), 3,4-epoxy-1-butene (1h), 1,2-epoxy-5-hexene (1i), 1,2-epoxy-9-decene (1j), (R)-(+)-styrene oxide ((R)-1g; 97% ee), cyclohexene oxide, 1,2-epoxy-3-methylpropane, and trans-stilbene oxide. Ethyl-2,3-epoxypropanoate was synthesized following a literature procedure of a similar compound (e.g., see (insert FN#1). (S)-1,2-Epoxy-3-phenoxypropane ((S)-1b) was synthesized using the Jacobsen kinetic resolution (>99.5% ee) (e.g., see (insert FN#2). Thin layer chromatography (TLC) was performed on DC-Fertigplatten SIL G-25 $UV_{254}$ pre-coated TLC plates. The developed chromatogram was visualized by UV lamp or stained using one of the following: aqueous potassium permanganate ($KMnO_4$) or ethanolic para-anisaldehyde. Selected purifications were performed using a Biotage Isolera One flash purification system, as noted in the experimental procedures.

Proton nuclear magnetic resonance ($^1H$ NMR) and carbon nuclear magnetic resonance ($^{13}C$ NMR) spectra were recorded on a Bruker-AVANCE 600 spectrometer (600 MHz) or Bruker-AVANCE 400 spectrometers (400 MHz) in deuterochloroform ($CDCl_3$) unless otherwise noted. Chemical shifts are recorded in parts per million (ppm) and are referenced to the centerline of deuterochloroform ($\delta$ 7.24 ppm $^1H$ NMR; $\delta$ 77.0 ppm $^{13}C$ NMR). Data was recorded as follows: chemical shift, multiplicity (s=singlet, d=doublet, t=tripet, q=quartet, qt=quintet, m=multiplet, br=broad). Coupling constants (J values) are given in Hertz (Hz). Infrared (IR) spectra were recorded on an Agilent Cary 630 FTIR. High resolution mass spectra (HRMS) were obtained on a Bruker Daltonics APEXIV 4.7 Tesla Fourier Transform Ion Cyclotron Resonance Mass Spectrometer (FT-ICR-MS) by Li Li of the Massachusetts Institute of Technology Department of Chemistry Instrumentation Facility. Gas chromatographic (GC) analysis was performed on an Agilent 7890A GC system on an Agilent HP-5 column (30 m, 0.32 mm i.d., 25 μm film thickness) with a flow rate of 1 ml/min using the following method: the oven temperature was held at 50° C. for 5 min and then increased linearly to 250° C. over 20 min with a final hold of 5 min.

Design and Construction of the Flow Apparatus:

FIG. 6 shows a Schematic of the continuous flow apparatus.

Figure 8A:
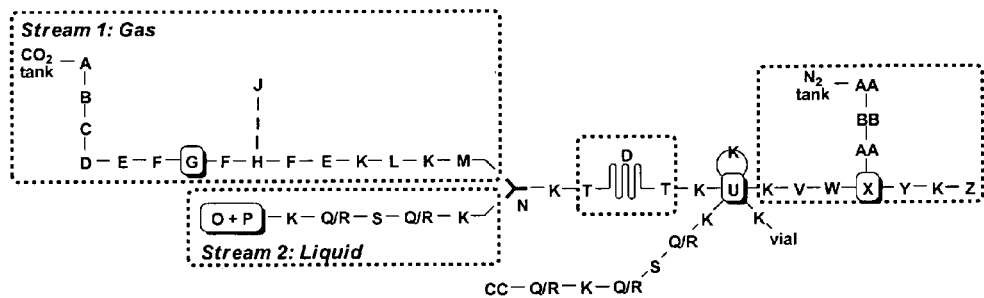
Figure 8B:
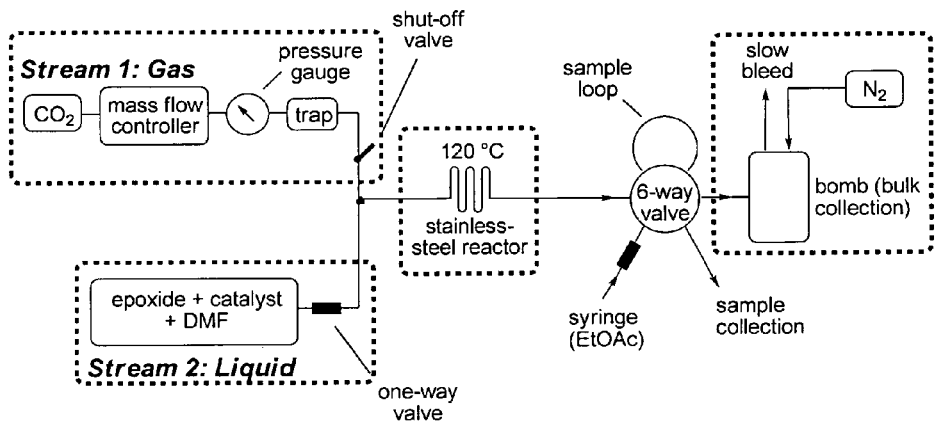

FIGS. 8A and 8B show a schematic of the continuous flow set-up, relating to Table S1 below.

TABLE S1

Continuous flow apparatus components and order of construction

| Item | Vendor | Part # | Part Description |
|---|---|---|---|
| A | Airgas | Y12215F320 | two stage brass 0-400 psi general regulator |
| B | Swagelok | SS-4-HRCG-2 | hex reducing coupling ¼" female NPT × ⅛" female NPT |
| C | Swagelok | SS-100-1-2 | tube fitting; male connector 1/16" tube OD × ⅛" male NPT |
| D | Upchurch Scientific | U-164 | stainless steel tubing 1/16" × 0.030" ID × 25 ft |
| E | Swagelok | SS-200-6-1 | tube fitting; reducing union ⅛" × 1/16" tube OD |
| F | McMaster-Carr | 89895K114 | SS Tubing ⅛" OD, .055" ID, .035" wall, 3" length |
| G | Sierra Instruments | C101-DD-1-OV1-SV1-PV2-V3-S3-C10 | mass flow controller |
| H | Swagelok | SS-200-3 | tube fitting; union tee ⅛" tube OD |
| I | Swagelok | SS-400-R-2 | tube fitting; reducer ¼" × ⅛" tube OD |
| J | Swagelok | PG1-63C-PG300-LAQX | 0-300 psi gauge; ¼" tube ADP lower mount |
| K | Upchurch Scientific | 1912L | Tubing, Teflon ® HPFA; .030" × 1/16" × 50 ft |
| L | First Cut | — | machined aluminum pressure vessel (trap) |
| M | Upchurch Scientific | P-732 | shut off valve |
| N | Upchurch Scientific | P-514 | Y-connector; 0.060" thru hole |
| O | Harvard Apparatus | 703305 | PHD Ultra Remote RS485 Infuse only syringe pump |
| P | Harvard Apparatus | 702267 | 8 mL stainless steel syringe with a 1/16" fitting |
| Q | Upchurch Scientific | P-255X | super flangeless nut, PEEK, natural |
| R | Upchurch Scientific | P-259X | super flangeless ferrule, 1/16", ETFE, yellow |
| S | Upchurch Scientific | CV-3330 | check valve |
| T | Swagelok | SS-100-6 | tube fitting, union, 1/16" tube OD |
| U | Upchurch Scientific | V-541 | 6-port injection valve |
| V | Swagelok | SS-102-1 | nut for 1/16" Swagelok tube fitting |
| W | Swagelok | SS-100-7-2 | tube fitting, female connector, 1/16" tube OD × ⅛" female NPT |
| X | Parr Instrument Company | 4790 Model No. 4793 | general purpose 100 mL pressure vessel (bomb) |
| Y | Swagelok | SS-200-6-1 | tube fitting, reducing union, ⅛" × 1/16" tube OD |
| Z | Upchurch Scientific | P-445 | micro metering valve |
| AA | Swagelok | SS-400-7-4 | tube fitting, female connector ¼" tube OD × ¼" female NPT |
| BB | McMaster-Carr | 5033K31 | Teflon ® PTFE ⅛" ID, ¼" OD, " 1/16 wall, semi-clear white |
| CC | Upchurch Scientific | P-628 | adapter, female slip luer to female, TEFZEL ® (ETFE) |

Flow Reactor Preparation and Execution:

First, the $CO_2$ tank was pressurized to ~20 psi higher than the desired back-pressure of the system (120 psi). The aluminum trap was pressurized and all the air expelled prior to the start of the reaction. To do this, the shut-off valve was closed and the mass flow controller set to purge. When the pressure gauge read the same value as the $CO_2$ tank regulator gauge, was fully pressurized. At this point the shut-off valve can be opened and closed to expel any air in the system. The back-pressure of the system (the nitrogen tank) was set to the desired pressure (~20 psi lower than that of the $CO_2$ tank, or 100 psi). An SGE syringe (10 mL) was filled with toluene and placed in the syringe pump. Once the back-pressure was set, the syringe pump was started (20 μL/min) and the mass flow controller was switched from purge to the desired setting (in sccm or mL/min). The system took approximately 15 minutes to equilibrate. During this time the reactor coil was brought to the desired temperature (120° C.) using a silicon oil bath, and the flow rates adjusted to obtain 1:1 v:v liquid/gas slug flow. The 6-way valve was in the LOAD position.

Once a steady flow rate was observed, the SGE syringe was removed, and a Harvard Apparatus stainless steel (8 mL) syringe containing the reaction solution was attached. The system then reached equilibrium. This was approximately four reactor volumes plus the volume of the reagent loop located on the 6-way valve. For example, if a reaction has a $t_R$ of 30 minutes, the equilibration time is approximately 2 h. When the system had reached its equilibrium, a collection vial was placed under the sample collection tube, and the 6-way valve was switched to the INJECT position. The vial was in place as the pressurized $CO_2$ in the reagent loop can expel some of the liquid rapidly. A syringe filled with ethyl acetate then pushed out any remaining product into the vial. After the sample was collected, the 6-way valve was switched back to LOAD. At this point, the parameters of the system may be changed and the process repeated. Quantitative conversion and yields were obtained as follows:

Conversion:

After collection of a sample from the 6-way valve, the tip of a pipette was used to remove ~2 μL and transfer the liquid to suitable vial. The vial was filled with ethyl acetate and GC analysis was performed. GC analysis provided quantitative data based on calibration graphs made using standardized solutions.

Yield:

Due to non-linear effects observed for the cyclic carbonate product on the GC instrument, $^1$H NMR was used to determine the yields of the products. After collection of a sample from the 6-way valve and removal of an aliquot for GC analysis, a known amount of the solution was accurately measured into a new vial. The solution was then diluted with ethyl acetate and water and brine added. After mixing the biphasic solution, a pipette was used to withdraw the organic layer, and filter it through a pipette containing sodium sulfate, into a 25 mL round-bottomed flask. The aqueous layer was extracted a further three times. The combined organic fractions were concentrated in vacuo to afford a brown liquid. A known amount of an external standard (trichloroethylene) was added to the round-bottomed flask, and the mixture was taken into $CDCl_3$ for $^1$H NMR analysis.

Batch Procedure for Cyclic Carbonate Formation:

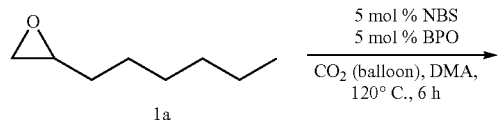

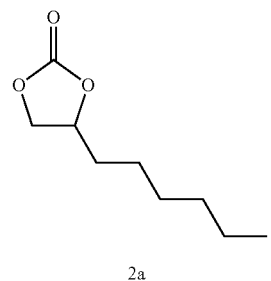

4-Hexyl-1,3-dioxolan-2-one (2a):

The atmosphere of a large, septa-sealed test-tube reaction flask containing a solution of 0.10 mL of 1,2-epoxyoctane (1a, 0.65 mmol), 5.8 mg of NBS (0.033 mmol), 7.9 mg of benzoyl peroxide (0.033 mmol), and 0.15 mL of dodecane (0.65 mmol) in 1.25 mL of N,N-dimethylacetamide (0.44 M) was flushed with carbon dioxide ($CO_2$) gas. A full balloon of $CO_2$ was then attached. The reaction mixture was heated to 120° C. and stirred for 6 h. The reaction mixture was cooled to rt and a small sample was removed for GC analysis. The remainder of the reaction mixture was poured into water and extracted three times with ethyl acetate. The combined organic fractions were washed four times with brine, dried over sodium sulfate, filtered, and concentrated by rotary evaporation in vacuo to afford a clear oil. The crude oil was purified by a Biotage flash purification system using a 10g silica gel column (hexanes:ethyl acetate gradient) to afford 0.083 g (75%) of the title compound 2a as a clear oil.

Representative Continuous Flow Procedure for Cyclic Carbonate Formation:

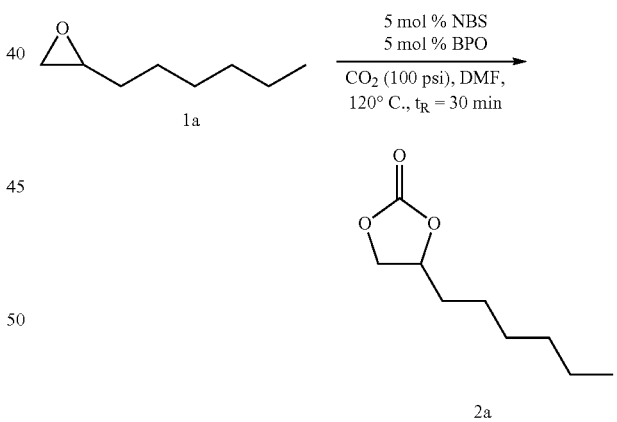

4-Hexyl-1,3-dioxolan-2-one (2a):

A 5 mL volumetric flask was charged with 1.5 mL of 1,2-epoxyoctane (1a, 10 mmol), 89 mg of NBS (0.5 mmol), 0.12 g of benzoyl peroxide (0.5 mmol), and 0.13 g of naphthalene (1.0 mmol). The volumetric flask was filled to the mark with anhydrous DMF (2 M). An 8 mL, stainless steel Harvard Apparatus syringe was filled with the solution and then attached to the flow apparatus (syringe pump). The flow apparatus itself was set up as described above. After approximately 4 $t_R$'s (~2 h), a sample was taken using the 6-way valve. The sample was analyzed by GC and $^1$H NMR. GC analysis indicated 96% conversion whereas $^1$H NMR analysis indicated a yield of 87% of the title compound 2a. IR (neat): 2928, 2859, 1788, 1384, 1165, 1059, 774 cm$^{-1}$. $^1$H NMR (400 MHz, CDCl$_3$): δ 4.67 (qd, J=7.5, 5.5 Hz, 1H), 4.50 (t, J=8.1 Hz, 1H), 4.04 (dd, J=8.3, 7.3 Hz, 1H), 1.79-1.73 (m, 1H), 1.68-1.61 (m, 1H), 1.45-1.27 (m, 10H), 0.86 (t, J=6.9 Hz, 3H). $^{13}$C NMR (100 MHz, CDCl$_3$): δ 155.1, 77.1, 69.4, 33.9, 31.5, 28.8, 24.3, 22.5. HRMS (DART) m/z calcd for C$_9$H$_{20}$NO$_3$ [M+NH$_4$]$^+$: 190.1438. Found: 190.1438.

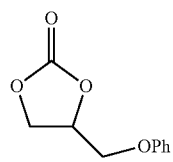

2b 4-(Phenoxymethyl)-1,3-dioxolan-2-one (2b):

1,2-Epoxy-3-phenoxy propane (1b, 1.4 mL, 10 mmol), NBS (89 mg, 0.50 mmol), benzoyl peroxide (0.12 g, 0.50 mmol), and naphthalene (0.13 g, 1.0 mmol) were combined in a 5 mL volumetric flask according to the representative procedure. GC and $^1$H NMR analysis of the final sample indicated 87% conversion and 86% yield to the title compound 2b. IR (solid film): 2927, 1783, 1600, 1490, 1396, 1161, 1081, 1009 cm$^{-1}$. $^1$H NMR (400 MHz, CDCl$_3$): δ 7.34-7.20 (m, 2H), 7.03-6.94 (m, 1H), 6.93-6.82 (m, 2H), 5.04-4.98 (m, 1H), 4.60 (t, J=8.4 Hz, 1H), 4.51 (dd, J=8.5, 5.9, 1H), 4.21 (dd, J=10.6, 4.2 Hz, 1H), 4.12 (dd, J=10.6, 3.6 Hz, 1H). $^{13}$C NMR (100 MHz, CDCl$_3$): δ 157.8, 154.7, 129.7, 122.0, 114.6, 74.1, 66.9, 66.3. HRMS (DART) m/z calcd for C$_{10}$H$_{14}$NO$_4$ [M+NH$_4$]$^+$: 212.0917. Found: 212.0916.

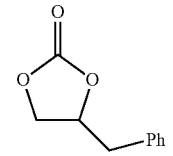

2c

4-Benzyl-1,3-dioxolan-2-one (2c):

(2,3-Epoxypropyl)benzene (1c, 1.3 mL, 10 mmol), NBS (89 mg, 0.50 mmol), benzoyl peroxide (0.12 g, 0.50 mmol) and naphthalene (0.13 g, 1.0 mmol) were combined in a 5 mL volumetric flask according to the representative procedure. GC and $^1$H NMR analysis of the final sample indicated 93% conversion and 90% yield to the title compound 2c. IR (neat): 2920, 1782, 1394, 1159, 1055 cm$^{-1}$. $^1$H NMR (400 MHz, CDCl$_3$): δ 7.33-7.23 (m, 3H), 7.21-7.15 (m, 2H), 4.89 (dq, J=13.3, 6.6 Hz, 1H), 4.39 (dd, J=8.6, 7.9 Hz, 1H), 4.12 (dd, J=8.6, 6.9 Hz, 1H), 3.09 (dd, J=14.2, 6.3 Hz, 1H), 2.95 (dd, J=14.2, 6.6 Hz, 1H). $^{13}$C NMR (100 MHz, CDCl$_3$): δ 154.9, 134.0, 129.4, 129.0, 127.6, 76.9, 68.6, 39.5. HRMS (DART) m/z calcd for C$_{10}$H$_{14}$NO$_3$ [M+NH$_4$]$^+$: 196.0968. Found: 196.0967.

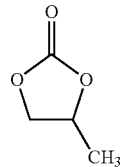

2d

Propylene Carbonate (2d):

Propylene oxide (1d, 0.70 mL, 10 mmol), NBS (89 mg, 0.50 mmol), benzoyl peroxide (0.12 g, 0.50 mmol), and naphthalene (0.13 g, 1.0 mmol) were combined in a 5 mL volumetric flask according to the representative procedure. $^1$H NMR analysis of the final sample indicated 81% yield to the title compound 2d. IR (neat): 2989, 1780, 1388, 1352, 1172, 1117, 1041, 774 cm$^{-1}$. $^1$H NMR (400 MHz, CDCl$_3$): δ 4.85-4.73 (m, 1H), 4.49 (dt, J=8.4, 7.3 Hz, 1H), 4.01-3.89 (m, 1H), 1.46-1.35 (m, 3H). $^{13}$C NMR (100 MHz, CDCl$_3$): δ 155.4, 73.9, 70.9, 19.5. HRMS (DART) m/z calcd for C$_4$H$_{10}$NO$_3$ [M+NH$_4$]$^+$: 120.0655. Found: 120.0658.

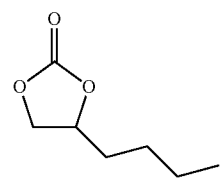

2e

4-Butyl-1,3-dioxolan-2-one (2e):

1,2-epoxyhexane (1e, 1.2 mL, 10 mmol), NBS (89 mg, 0.50 mmol), benzoyl peroxide (0.12 g, 0.50 mmol), and naphthalene (0.13 g, 1.0 mmol) were combined in a 5 mL volumetric flask according to the representative procedure. $^1$H NMR analysis of the final sample indicated 83% yield to the title compound 2e. IR (neat): 2932, 2867, 1785, 1384, 1166, 1058, 774 cm$^{-1}$. $^1$H NMR (400 MHz, CDCl$_3$): δ 4.68 (qd, J=7.5, 5.6 Hz, 1H), 4.50 (t, J=8.1 Hz, 1H), 4.04 (dd, J=8.3, 7.3 Hz, 1H), 1.86-1.72 (m, 1H), 1.69-1.62 (m, 1H), 1.51-1.27 (m, 4H), 0.90 (t, J=7.0 Hz, 3H). $^{13}$C NMR (100 MHz, CDCl$_3$): δ 155.1, 69.4, 33.6, 26.5, 22.3, 13.8. HRMS (DART) m/z calcd for C$_7$H$_{16}$NO$_3$ [M+NH$_4$]$^+$: 162.1125. Found: 162.1124.

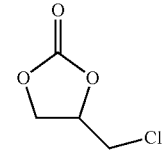

2f 4-(Chloromethyl)-1,3-dioxolan-2-one (2f):

Epichlorohydrin (1f, 0.78 mL, 10 mmol), NBS (89 mg, 0.50 mmol), benzoyl peroxide (0.12 g, 0.50 mmol), and naphthalene (0.13 g, 1.0 mmol) were combined in a 5 mL volumetric flask according to the representative procedure. $^1$H NMR analysis of the final sample indicated 78% yield to the title compound 2f. IR (neat): 2967, 1779, 1395, 1158, 1066 cm$^{-1}$. $^1$H NMR (400 MHz, CDCl$_3$): δ 5.02-4.90 (m, 1H), 4.55 (t, J=8.6 Hz, 1H), 4.35 (dd, J=8.9, 5.7 Hz, 1H), 3.78 (dd, J=12.3, 4.9 Hz, 1H), 3.68 (dd, J=12.3, 3.6 Hz, 1H). $^{13}$C NMR (100 MHz, CDCl$_3$): δ 154.5, 74.5, 67.0, 44.1. HRMS (DART) m/z calcd for C$_4$H$_9$NO$_3$Cl [M+NH$_4$]$^+$: 154.0265. Found: 154.0259.

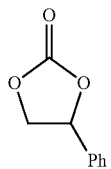

2g

4-Phenyl-1,3-dioxolan-2-one (2g):

Styrene oxide (1 g, 1.1 mL, 10 mmol), NBS (89 mg, 0.50 mmol), benzoyl peroxide (0.12 g, 0.50 mmol), and naphthalene (0.13 g, 1.0 mmol) were combined in a 5 mL volumetric flask according to the representative procedure. $^1$H NMR analysis of the final sample indicated 72% yield to the title compound 2g. IR (neat): 1784, 1670, 1160, 1050 cm$^{-1}$. $^1$H NMR (400 MHz, CDCl$_3$): δ 7.44-7.36 (m, 3H), 7.36-7.28 (m, 2H), 5.64 (t, J=8.0 Hz, 1H), 4.7867 (t, J=8.4 Hz, 1H), 4.30 (dd, J=8.6, 7.9 Hz, 1H). $^{13}$C NMR (100 MHz, CDCl$_3$): δ 154.9, 135.8, 129.8, 129.3, 125.9, 78.0, 71.2. HRMS (DART) m/z calcd for C$_9$H$_{12}$NO$_3$ [M+NH$_4$]$^+$: 182.0812. Found: 182.0810.

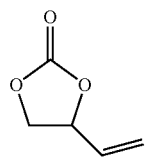

2h

4-Vinyl-1,3-dioxolan-2-one (2h):

3,4-Epoxybutene (1h, 0.81 mL, 10 mmol), NBS (90 mg, 0.50 mmol), benzoyl peroxide (0.12 g, 0.50 mmol), and naphthalene (0.13 g, 1.0 mmol) were combined in a 5 mL volumetric flask according to the representative procedure. $^1$H NMR analysis of the final sample indicated 52% yield to the title compound 2h. IR (neat): 2992, 1781, 1384, 1325, 1159, 1052, 770 cm$^{-1}$. $^1$H NMR (400 MHz, CDCl$_3$): δ 5.85 (ddd, J=17.3, 10.4, 6.9 Hz, 1H), 5.45 (dd, J=17.1, 6.8 Hz, 1H), 5.38 (dd, J=10.4, 0.7, 1H), 5.08 (q, J=7.5 Hz, 1H), 4.55 (t, J=8.3 Hz, 1H), 4.10 (t, J=8.0 Hz, 1H). $^{13}$C NMR (100 MHz, CDCl$_3$): δ 155.0, 132.4, 121.3, 77.5, 69.2. HRMS (DART) m/z calcd for C$_5$H$_{10}$NO$_3$ [M+NH$_4$]$^+$: 132.0655. Found: 132.0653.

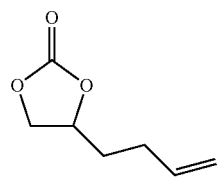

2i 4-(But-3-en-1-yl)-1,3-dioxolan-2-one (2i):

1,2-Epoxy-5-hexene (1i, 1.1 mL, 10 mmol), NBS (89 mg, 0.50 mmol), benzoyl peroxide (0.12 g, 0.50 mmol), and naphthalene (0.13 g, 1.0 mmol) were combined in a 5 mL volumetric flask according to the representative procedure. $^1$H NMR analysis of the final sample indicated 58% yield to the title compound 2i. IR (neat): 1783, 1384, 1165, 1056, 914, 773 cm$^{-1}$. $^1$H NMR (400 MHz, CDCl$_3$): δ 5.72 (ddt, J=17.0, 10.2, 6.7 Hz, 1H), 5.07-4.91 (m, 2H), 4.67 (qd, J=7.7, 5.2 Hz, 1H), 4.47 (t, J=8.2 Hz, 1H), 4.02 (dd, J=8.5, 7.2 Hz, 1H), 2.29-1.99 (m, 2H), 1.85 (dtd, J=14.1, 8.1, 5.9 Hz, 1H), 1.78-1.61 (m, 1H). $^{13}$C NMR (100 MHz, CDCl$_3$): δ 155.2, 136.3, 116.5, 76.6, 69.5, 33.2, 28.8. HRMS (DART) m/z calcd for C$_7$H$_{14}$NO$_3$ [M+NH$_4$]$^+$: 160.0968. Found: 160.0968.

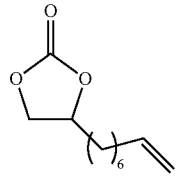

2j 4-(oct-7-en-1-yl)-1,3-dioxolan-2-one (2j):

1,2-Epoxy-9-decene (1j, 1.8 mL, 10 mmol), NBS (89 mg, 0.50 mmol), benzoyl peroxide (0.12 g, 0.50 mmol), and naphthalene (0.13 g, 1.0 mmol) were combined in a 5 mL volumetric flask according to the representative procedure. $^1$H NMR analysis of the final sample indicated 51% yield to the title compound 2j. IR (neat): 2927, 2857, 1790, 1385, 1163, 1059, 909 cm$^{-1}$. $^1$H NMR (400 MHz, CDCl$_3$): δ 5.73 (ddt, J=16.9, 10.2, 6.7 Hz, 1H), 4.93 (ddd, J=17.1, 3.6, 1.6, 1H), 4.87 (ddt, J=10.2, 2.2, 1.2 Hz, 1H), 4.64 (qd, J=7.5, 5.4 Hz, 1H), 4.47 (d, J=8.0 Hz, 1H), 4.00 (dd, J=8.4, 7.2 Hz, 1H), 2.04-1.94 (m, 2H), 1.79-1.68 (m, 1H), 1.68-1.56 (m, 1H), 1.51-1.14 (m, 8H). $^{13}$C NMR (100 MHz, CDCl$_3$): δ 155.3, 139.0, 114.5, 77.3, 69.6, 34.0, 33.8, 29.1, 28.9, 28.8. HRMS (DART) m/z calcd for C$_{11}$H$_{22}$NO$_3$ [M+NH$_4$]$^+$: 216.1594. Found: 216.1589.

Solvent Studies:

TABLE S3

Solvent screen

| entry | solvent$^a$ | conversion | yield (%)$^b$ | notes |
|---|---|---|---|---|
| 1 | THF | — | — | |
| 2 | acetonitrile | — | — | |
| 3 | toluene | — | — | NBS not |
| 4 | DMF | 100 | 99 | |
| 5 | DMA | 100 | 96 | |
| 6 | NMP | 43 | 53 | |
| 7 | DMSO | 21 | 16 | |
| 8 | hexanes | — | — | NBS not |
| 9 | MeOH | — | — | |
| 10 | EtOH | — | — | |
| 11 | acetone | — | — | |

TABLE S3-continued

| 12 | EtOAc | — | — |
| 13 | propylene carbonate | — | — |

[a] An abbreviation listing can be found at the end of this example.
[b] Determined by GC analysis.

Analysis of Enantiopure Epoxides:

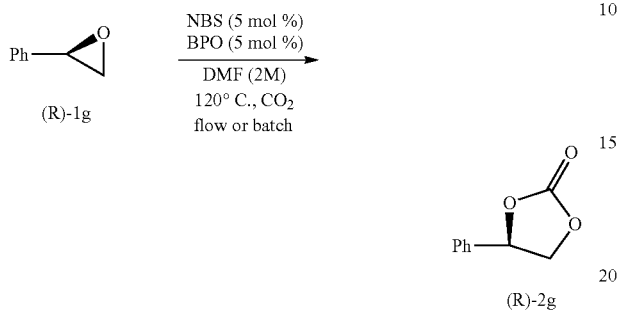

Reactions were conducted in both flow and batch conditions, and the ee of the product in each case was determined by chiral HPLC measurement using ChiralCel OD, 10% IPA/hexanes, 1 mL/min, $t_R$=13.2 min, $t_S$=15.2 min. Partial racemization of the products relative to the starting materials was observed under both flow and batch conditions (flow 76% ee; batch 50% ee).

Reactions were conducted in both flow and batch conditions, and ee of the product in each case was determined by chiral HPLC measurement using ChiralCel AD, 6% IPA/hexanes, 1 mL/min, $t_R$=29.6 min, $t_S$=28.7 min. The enantioenrichment of the starting epoxide was full transferred into the carbonate product under both flow and batch conditions (flow >99% ee; batch >99% ee).

Kinetics Experiments:

CHART 1

Kinetic order with respect to the concentration of epoxide.

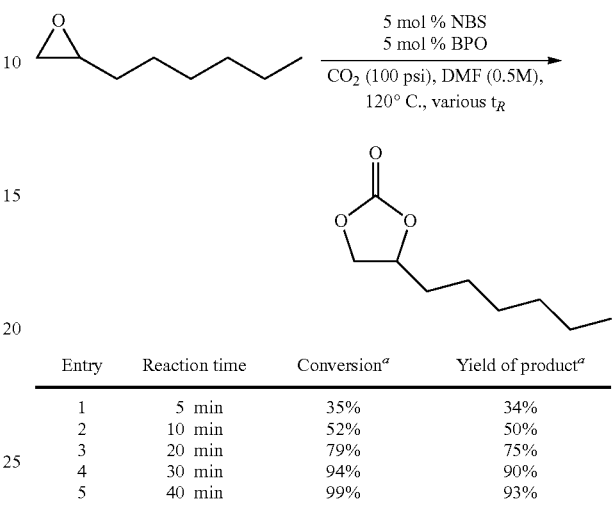

| Entry | Reaction time | Conversion[a] | Yield of product[a] |
|---|---|---|---|
| 1 | 5 min | 35% | 34% |
| 2 | 10 min | 52% | 50% |
| 3 | 20 min | 79% | 75% |
| 4 | 30 min | 94% | 90% |
| 5 | 40 min | 99% | 93% |

$$\text{rate} = -\frac{d[\text{epoxide}]}{dt} = k_{obs}[\text{epoxide}]$$

$$\ln[\text{epoxide}]_t = \ln[\text{epoxide}]_o - k_{obs}t$$

Based on the kinetic study, the reaction was determined to most likely be first order with respect to the concentration of epoxide.

CHART 2

Kinetic order with respect to benzoyl peroxide (BPO; initiator):

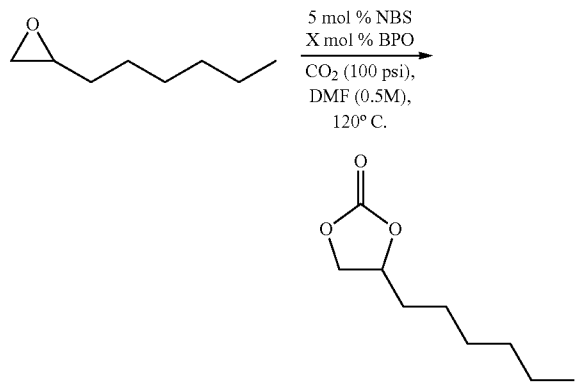

$$\text{rate} = -\frac{d[\text{epoxide}]}{dt}$$
$$= k_{obs}[\text{epoxide}]$$

$$\ln[\text{epoxide}]_t = \ln[\text{epoxide}]_o - k_{obs}t$$

Zero order reaction with respect to BPO: $k_{obs}$ is independent to [BPO]

CHART 3

Kinetic order with respect to N-bromosuccinimide (NBS; catalyst):

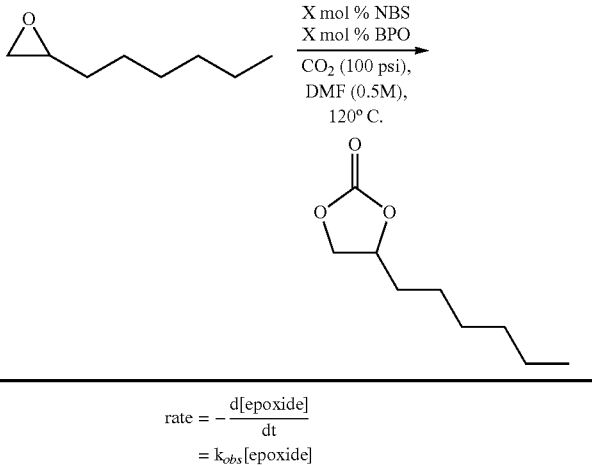

$$\text{rate} = -\frac{d[\text{epoxide}]}{dt}$$

$$= k_{obs}[\text{epoxide}]$$

$$\ln[\text{epoxide}]_t = \ln[\text{epoxide}]_o - k_{obs}t$$

First order reaction with respect to NBS: $k_{obs} \propto [\text{NBS}]$

CHART 4

Effect of $CO_2$ pressure on the yield of the reaction.

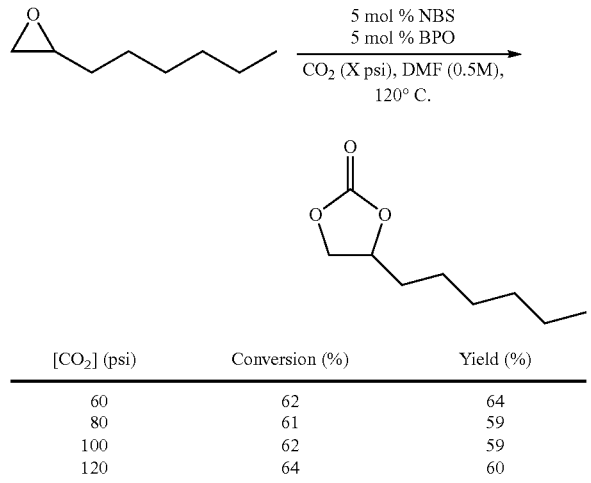

| [CO$_2$] (psi) | Conversion (%) | Yield (%) |
|---|---|---|
| 60 | 62 | 64 |
| 80 | 61 | 59 |
| 100 | 62 | 59 |
| 120 | 64 | 60 |

The pressure of the $CO_2$ (between pressures of 60 and 120 psi) did not significantly affect the final concentration of the epoxide (or the overall yield of the reaction).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:
1. A method, comprising:
reacting a compound of Formula (I):

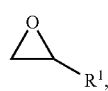
(I)

with $CO_2$ in the presence of a catalyst to produce a compound of Formula (II):

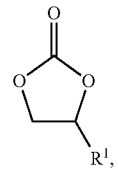
(II)

wherein $R^1$ is optionally substituted alkyl, optionally substituted cycloalkyl, optionally substituted heteroalkyl, optionally substituted heteroalkyl, optionally substituted aryl-alkyl, optionally substituted aryl-O-alkyl, optionally substituted aryl, optionally substituted heteroaryl, or optionally substituted alkenyl, and wherein the catalyst comprises an electrophilic halogen.

2. The method of claim 1, wherein the reacting is carried out in the presence of a catalyst comprising an amide.

3. The method of claim 2, wherein the reacting is carried out in the presence of an oxidant.

4. The method of claim 3, wherein the oxidant also functions as a solvent.

5. The method of claim 1, wherein the electrophilic halogen is an electrophilic chlorine, electrophilic bromine, or electrophilic iodine.

6. The method of claim 5, wherein the catalyst comprising an electrophilic bromine is NBS.

7. The method of claim 1, wherein the reacting is carried out in the presence of a solvent.

8. The method of claim 7, wherein the solvent is DMF, DMA, NMP, or combinations thereof.

9. The method of claim 3, wherein the oxidant is DMF, DMA, NMP, or combinations thereof.

10. The method of claim 1, wherein the reacting is carried out in a flow reactor.

11. The method of claim 1, wherein the reaction is carried out under conditions suitable for forming a compound of Formula (II) in a percent conversion of greater than about 60% in a period of time of less than about 24 hours.

12. The method of claim 1, wherein the compound of Formula (II) is chiral.

13. The method of claim 1, wherein the compound of Formula (II) has an enantiomeric excess greater than about 80%.

14. The method of claim 1, wherein the reaction is a gas-liquid biphasic reaction.

15. The method of claim 1, wherein the reacting is not conducted in the presence of a solid support.

16. The method of claim 1, wherein no portion of the catalyst is associated with a solid support.

17. The method of claim 1, wherein the reaction is carried out under conditions suitable for forming a compound of Formula (II) in a percent conversion of greater than about 70% in a period of time of less than about 12 hours.

18. The method of claim 1, wherein the reaction is carried out under conditions suitable for forming a compound of Formula (II) in a percent conversion of greater than about 80% in a period of time of less than about 6 hours.

19. The method of claim 1, wherein the reaction is carried out under conditions suitable for forming a compound of Formula (II) in a percent conversion of greater than about 90% in a period of time of less than about 1 hour.

20. The method of claim 1, wherein the reaction is carried out under conditions suitable for forming a compound of Formula (II) in a percent yield of greater than about 70% in a period of time of less than about 1 hour.

* * * * *